(12) United States Patent
Mendez et al.

(10) Patent No.: US 7,642,246 B2
(45) Date of Patent: Jan. 5, 2010

(54) PURE ROCURONIUM BROMIDE

(75) Inventors: Juana Araceli Mendez, Coyoacan (MX); Marco A. De La Mora, Capultitlan (MX); Alejandro Guillen, Xonacatlan (MX); Hugo Herrera, Ampliacion Izcalli Ecatepec (MX)

(73) Assignee: Sicor Inc., Irvine, CA (US)

( * ) Notice: Subject to any disclaimer, the term of this patent is extended or adjusted under 35 U.S.C. 154(b) by 0 days.

(21) Appl. No.: 11/521,197

(22) Filed: Sep. 13, 2006

(65) Prior Publication Data

US 2007/0265237 A1 Nov. 15, 2007

Related U.S. Application Data

(60) Provisional application No. 60/784,746, filed on Mar. 21, 2006, provisional application No. 60/776,322, filed on Feb. 23, 2006, provisional application No. 60/752,435, filed on Dec. 20, 2005, provisional application No. 60/752,671, filed on Dec. 19, 2005, provisional application No. 60/717,122, filed on Sep. 13, 2005.

(51) Int. Cl.
*A01N 45/00* (2006.01)
*C07D 215/04* (2006.01)

(52) U.S. Cl. ............................ 514/26; 540/2

(58) Field of Classification Search ........................ None
See application file for complete search history.

(56) References Cited

U.S. PATENT DOCUMENTS

| | | | |
|---|---|---|---|
| 3,553,212 A | 1/1971 | Hewett et al. | |
| 4,447,425 A | 5/1984 | Carlyle et al. | |
| 4,894,369 A | 1/1990 | Sleigh et al. | |
| 5,591,735 A | 1/1997 | Tuba et al. | |
| 5,808,051 A | 9/1998 | Magni et al. | |
| 5,817,803 A * | 10/1998 | Magni et al. | 540/96 |
| 6,090,957 A | 7/2000 | Magni et al. | |
| 2005/0159398 A1 | 7/2005 | Adar et al. | |
| 2006/0009485 A1 | 1/2006 | Friedman et al. | |
| 2006/0058275 A1 | 3/2006 | Friedman et al. | |
| 2006/0058276 A1 | 3/2006 | Friedman et al. | |

2007/0117975 A1 5/2007 Mendez et al.

FOREIGN PATENT DOCUMENTS

| | | |
|---|---|---|
| EP | 0 287 150 A1 | 10/1988 |
| EP | 0 287 150 B1 | 10/1988 |
| EP | 0 288 102 A1 | 10/1988 |
| EP | 0 608 495 A2 | 8/1994 |
| KR | 20070083226 A | 8/2007 |
| WO | WO-2005/068487 A2 | 7/2005 |
| WO | WO 2005/068487 A2 | 7/2005 |
| WO | WO-2007/073424 | 6/2007 |

OTHER PUBLICATIONS

Tuba et al. Current Medicinal Chemistry, 2002, 9(16), 1507-36.*
Tempe et al. Journal of Anaethesiology, 2005, 21(2), 159-164.*
Gao et al. British Journal of Anaesthesia, 2002, 88(6), 764-70.*
Naguib et al. British Journal of Anaesthesia, 1995, 75, 588-92.*
Strobel, H.A. & Heineman, W.R., Chemical Instrumentation: A Systematic Approach 922, 953 (3d ed., Wiley & Sons, New York 1989).
International Search Report and Written Opinion of the International Searching Authority for PCT/US2006/035828.
Buckett, W. R., et al., "Pancuronium Bromide and Other Steroidal Neuromuscular Blocking Agents Containing Acetylcholine Fragments", Journal of Medicinal Chemistry, 1973, vol. 16, No. 10, pp. 1116-1124.
PCT International Search Report and Written Opinion of the International Searching Authority for PCT/US2006/035948 dated Dec. 17, 2007.
Cameron, Kenneth S., et al., Magnetic Resonance in Chemistry, 2002, vol. 40, pp. S106-S109.
Cameron, Kenneth S., et al., Organic Letters, 2002, vol. 4, No. 20, pp. 3403-3406.
Cameron, Kenneth S., et al., Magnetic Resonance in Chemistry, 2002, vol. 40, No. 4, pp. 251-260.
Adam, Julia M., et al., Journal of Medicinal Chemistry, 2002, vol. 45, No. 9, pp. 1806-1816.
Van Montfoort, Jessica E., et al., Journal of Pharmacology and Experimental Therapeutics, 2001, vol. 298, No. 1, pp. 110-115.
Gutteck-Amsler, Ursula, et al., Clinical Chemistry, 2000, vol. 46, No. 9, pp. 1413-1414.

* cited by examiner

*Primary Examiner*—James O Wilson
*Assistant Examiner*—Noble Jarrell
(74) *Attorney, Agent, or Firm*—Kenyon & Kenyon LLP

(57) ABSTRACT

Disclosed herein is rocuronium bromide having a potentiometrical assay of from 99% to 101% in acetic acid and perchloric acid, having less than about 0.2% area by HPLC of 2β-(4-morpholinyl)-16β-(1-pyrrolidinyl)-5α-androstan-3α-ol-17β-acetate, and having at least one of the solvents ethyl ether and dichloromethane in an amount equal to or less than about 850 ppm, and 600 ppm, respectively.

8 Claims, No Drawings

PURE ROCURONIUM BROMIDE

RELATED APPLICATIONS

This application claims the benefit of U.S. provisional application Ser. Nos. 60/717,122, filed on Sep. 13, 2005; 60/752,671, filed on Dec. 19, 2005; 60/752,435, filed on Dec. 20, 2005; 60/776,322, filed on Feb. 23, 2006; and 60/784,746, filed on Mar. 21, 2006, herein incorporated by reference.

FIELD OF THE INVENTION

The invention encompasses substantially pure rocuronium bromide, Compound I.

BACKGROUND OF THE INVENTION

1-[17β-(acetyloxy)-3α-hydroxy-2β-(4-morpholinyl)-5α-androstan-16β-yl]-1-(2-propenyl)pyrrolidinium bromide (rocuronium bromide, Compound I) has the following structure

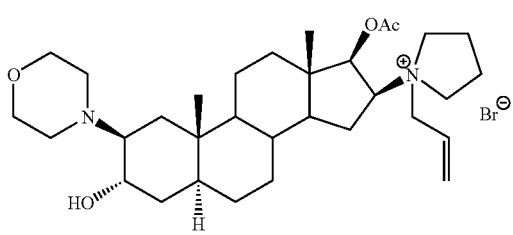

and a formula of $C_{32}H_{53}BrN_2O_4$ and a molecular weight of 609.70. Rocuronium bromide is used as a nondepolarizing neuromuscular blocking agent with a rapid to intermediate onset depending on dose and intermediate duration. It acts by competing for cholinergic receptors at the motor end-plate. This action is antagonized by acetylcholinesterase inhibitors, such as neostigmine and edrophonium.

Rocuronium Bromide is marketed in North America under the name ZEMURON®, and elsewhere under the brand name ESMERON®. It is supplied as a sterile, nonpyrogenic, isotonic solution that is clear, colorless to yellow/orange, for intravenous injection only.

The preparation of rocuronium bromide is disclosed in U.S. Pat. Nos. 5,817,803 and 4,894,369, and in U.S. publication No. 2005/0159398.

U.S. Pat. No. 4,894,369 ("'369 patent") discloses the preparation of rocuronium bromide which is purified by chromatography followed by crystallization from dichloromethane and ether.

U.S. publication No. 2005/0159398 discloses rocuronium bromide made via a bis-acetylated intermediate, wherein Rocuronium is obtained in yields of about 87% and in a purity of 98% area by HPLC.

Like any synthetic compound, rocuronium bromide salt can contain extraneous compounds or impurities that can come from many sources such as degradation. The extraneous compounds or impurities can be unreacted starting materials, synthetic by-products, products of side reactions, and/or degradation products. Impurities in rocuronium bromide salt or any active pharmaceutical ingredient (API) are undesirable and, in extreme cases, might even be harmful to a patient being treated with a dosage form containing the API.

In addition to stability, which is a factor in the shelf life of the API, the purity of the API produced in the commercial manufacturing process is clearly a necessary condition for commercialization. Impurities introduced during commercial manufacturing processes must be limited to very small amounts, and are preferably substantially absent. For example, the International Conference on Harmonisation of Technical Requirements for Registration of Pharmaceuticals for Human Use (ICH Q7A Good Manufacturing Practice Guidance for Active Pharmaceutical Ingredients, dated Nov. 10, 2000) requires that process impurities be maintained below set limits by specifying the quality of raw materials, controlling process parameters, such as temperature, pressure, time, and stoichiometric ratios, and including purification steps, such as crystallization, distillation, and liquid-liquid extraction, in the manufacturing process.

The product mixture of a chemical reaction is rarely a single compound with sufficient purity to comply with pharmaceutical standards. Side products and by-products of the reaction and adjunct reagents used in the reaction will, in most cases, also be present in the product mixture. At certain stages during processing of the API, Rocuronium bromide, it must be analyzed for purity, typically, by HPLC, TLC or GC analysis, to determine if it is suitable for continued processing and, ultimately, for use in a pharmaceutical product. The API need not be absolutely pure, as absolute purity is a theoretical ideal that is typically unattainable. Rather, purity standards are set with the intention of ensuring that an API is as free of impurities as possible, and, thus, are as safe as possible for clinical use. As discussed above, in the United States, the Food and Drug Administration guidelines recommend that the amounts of some impurities be limited to less than 0.1 percent.

Generally, side products, by-products, and adjunct reagents (collectively "impurities") are identified spectroscopically and/or with another physical method, and then associated with a peak position, such as that in a chromatogram, or a spot on a TLC plate. (Strobel p. 953, Strobel, H. A.; Heineman, W. R., Chemical Instrumentation: A Systematic Approach, (3rd ed., Wiley & Sons, New York 1989)). Thereafter, the impurity can be identified, e.g., by its relative position in the chromatogram, where the position in a chromatogram is conventionally measured in minutes between injection of the sample on the column and elution of the particular component through the detector. The relative position in the chromatogram is known as the "retention time."

The retention time can vary about a mean value based upon the condition of the instrumentation, as well as many other factors. To mitigate the effects such variations have upon accurate identification of an impurity, practitioners use the "relative retention time" ("RRT") to identify impurities. (Strobel p. 922). The RRT of an impurity is its retention time divided by the retention time of a reference marker. It may be advantageous to select a compound other than the API that is added to, or present in, the mixture in an amount sufficiently large to be detectable and sufficiently low as not to saturate the column, and to use that compound as the reference marker for determination of the RRT.

As is known by those skilled in the art, the management of process impurities is greatly enhanced by understanding their chemical structures and synthetic pathways, and by identifying the parameters that influence the amount of impurities in the final product.

According to the European pharmacopoeia rocuronium bromide should contain not more than 0.2% area by HPLC of impurity A. In addition according to the ICH guide lines (Q3C Impurities: Tables and list, November 2003) rocuronium bromide should contain no more than about 5000 ppm of ethyl ether, and 600 ppm of dichloromethane. The invention encompasses rocuronium bromide that exceeds the limitations set forth by the European Pharmacopoeia 5th edition (Supplement 5.4, pp. 4013-4014) and ICH guidelines.

Like any synthetic compound, rocuronium bromide can contain extraneous compounds and/or impurities that can come from many sources. They can be unreacted starting materials, by-products of the reaction, products of side reactions, or degradation products. The invention addresses these issues by providing rocuronium bromide in high purity.

SUMMARY OF THE INVENTION

An embodiment of the invention encompasses rocuronium bromide, Compound I.

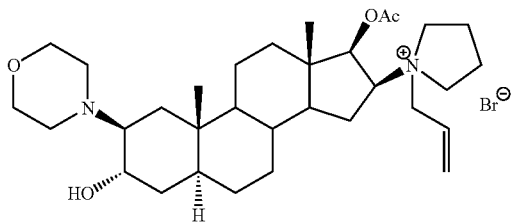

having a potentiometrical assay of from 99% to 101% in acetic acid and perchloric acid, having less than about 0.2% area by HPLC of impurity A, and having at least one of the solvents ethyl ether and dichloromethane in an amount equal to or less than about 850 ppm, and 600 ppm, respectively. Preferably, the rocuronium bromide has less than about 0.1% area by HPLC of impurity A, more preferably, about 0.1% area to about 0.02% area by HPLC of impurity A, and, most preferably, about 0.07% area to about 0.02% area by HPLC of impurity A. Preferably, the rocuronium bromide has a purity of about 99% to about 100% area by HPLC. Preferably, the rocuronium bromide has a total solvent content of less than 2000 ppm.

Another embodiment of the invention encompasses a pharmaceutical formulation comprising the rocuronium bromide, and at least one pharmaceutically acceptable excipient.

Another embodiment of the invention encompasses a process for preparing the pharmaceutical formulation comprising mixing the rocuronium bromide and the at least one pharmaceutically acceptable excipient.

Yet another embodiment of the invention encompasses a method of inducing muscle relaxation comprising administering the pharmaceutical formulation of claim 6 to a patient in need thereof.

DETAILED DESCRIPTION OF THE INVENTION

As used herein, the term "substantially pure" when referring to Rocuronium bromides, relates to Rocuronium bromide with a potentiometrical assay from 99 to 101% in acetic acid and perchloric acid, with less than about 0.2% area by HPLC of impurity A, and with at least one of the solvents: ethyl ether and dichloromethane in an amount of equal or less than about 850 ppm, and 600 ppm, respectively.

The invention encompasses a process for preparing substantially pure rocuronium bromide. In part, the process reduces the amount of pyrrolidine used during the rocuronium bromide synthesis which in turn reduces the amount of undesired by-products. Also, in the process the work-up procedure during the rocuronium bromide synthesis reduces the amount of residual solvents in the product to a level acceptable by the European pharmacopoeia and ICH guidelines standards.

Example 23 of the '369 patent discloses the preparation of rocuronium bromide by a reaction of (2α,3α,5α,16β,17β)-2-(4-morpholinyl)-16-(1-pyrrolidinyl)-androstane-3,17-diol 17-acetate and 8.1 equivalents of allyl bromide. The reaction usually takes 22 hours under pressure at room temperature. See '369 patent, col. 8, ll. 27-46. Comparative Example 1 below repeated the process disclosed in the '369 patent, and illustrates that the process provides rocuronium bromide having 16519 ppm of ethyl ether and 176 ppm of dichloromethane. Hence, the process disclosed in Example 23 of the '369 patent yields rocuronium bromide that contains residual solvents in excess of those allowed by the ICH guidelines purity standards, even though the process utilized purification by chromatography followed by crystallization.

The process of the invention yields rocuronium bromide that meets the European pharmacopoeia and ICH guidelines purity standards without the additional purification steps required in the prior art.

As used herein, unless otherwise indicated, the term "wet" as applied to a product refers to a product containing more than about 850 ppm of ethyl ether and 600 ppm of dichloromethane.

As used herein, unless otherwise indicated, the term "impurity A" refers to 2β-(4-morpholinyl)-16β-(1-pyrrolidinyl)-5α-androstan-3α-ol-17β-acetate, Compound VIII.

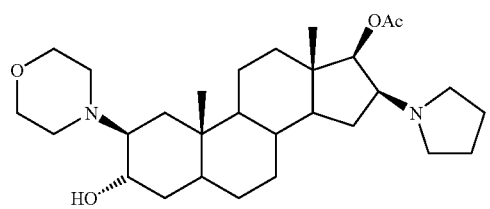

An embodiment of the invention encompasses substantially pure rocuronium bromide, Compound I.

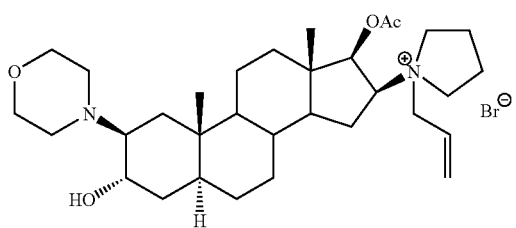

Preferably, the rocuronium bromide has a potentiometrical assay from 99 to 101% in acetic acid and perchloric acid, with less than about 0.1% area by HPLC of impurity A and with at least one of the solvents ethyl ether and dichloromethane in an amount of equal or less than about 850 ppm, and 600 ppm, respectively. More preferably, the rocuronium bromide has a potentiometrical assay from 99 to 101% in acetic acid and perchloric acid, with about 0.1% area to about 0.02% area by HPLC of impurity A, and with at least one of the solvents ethyl ether and dichloromethane in an amount of equal or less than about 850 ppm, and 600 ppm, respectively. Most preferably, the rocuronium bromide has a potentiometrical assay from 99 to 101% in acetic acid and perchloric acid, with about 0.07% area to about 0.02% area by HPLC of impurity A, and with at least one of the solvents ethyl ether and dichloromethane in an amount of equal or less than about 850 ppm, and 600 ppm, respectively.

Preferably, the rocuronium bromide has a purity of about 99% to about 100% area by HPLC.

Preferably, the rocuronium bromide has a total solvent content of less than 2000 ppm.

The HPLC used is according to the European Pharmacopoeia HPLC method reported in the European Pharmacopoeia 5th edition (Supplement 5.4, pp. 4013-4014).

The invention further encompasses a process for preparing substantially pure rocuronium bromide, Compound I, comprising: combining 2β-(4-morpholinyl)-16β-(1-pyrrolidinyl)-5α-androstan-3α-ol-17β-acetate (Compound VIII),

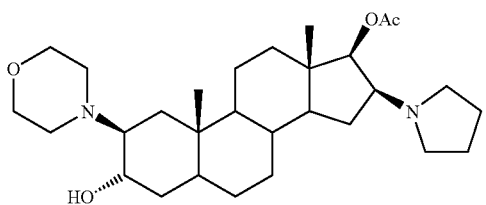

a polar aprotic organic solvent, about 1.3 to about 3 equivalents of allyl bromide per mole of Compound VIII and an inorganic base; isolating rocuronium bromide; dissolving the isolated rocuronium bromide in a polar aprotic organic solvent; adding a decolorizing agent optionally combined with a base; filtering the mixture to obtain a filtrate; adding the filtrate to an anti-solvent and stirring at about 840 rpm to 1000 rpm to obtain a suspension; recovering wet solid of rocuronium bromide; and drying the wet rocuronium bromide at a temperature of no more than about 35° C.

Rocuronium bromide with a potentiometrical assay from 99 to 101% in acetic acid and perchloric acid, with less than about 0.1% area by HPLC of impurity A, and with at least one of the solvents ethyl ether and dichloromethane in an amount of equal or less than about 850 ppm, and 600 ppm, respectively, can be prepared by combining 2β-(4-morpholinyl)-16β-(1-pyrrolidinyl)-5α-androstan-3α-ol-17β-acetate (Compound VIII), about 1.3 to about 3 equivalents of allyl bromide per mole of Compound VIII, and a polar aprotic organic solvent, wherein their water content is of less than about 0.1% by KF, and an inorganic base; isolating rocuronium bromide; dissolving Rocuronium bromide of formula I in a polar aprotic organic solvent; removing the polar aprotic organic solvent at a temperature below about 22° C. to obtain an oily residue; dissolving the oily residue in a polar aprotic organic solvent; adding a decolorizing agent optionally combined with a base to form a mixture; filtering the mixture to obtain a filtrate; adding the filtrate to an anti-solvent and stirring at about 840 rpm to 1000 rpm to obtain a suspension; recovering the wet solid of Rocuronium bromide of formula I from the suspension; and drying the Rocuronium bromide at a temperature of no more than about 35° C.

Rocuronium bromide with a potentiometrical assay from 99 to 101% in acetic acid and perchloric acid, with about 0.1% area to about 0.02% area by HPLC of impurity A, and with at least one of the solvents ethyl ether and dichloromethane in an amount of equal or less than about 850 ppm, and 600 ppm, respectively, can be prepared by combining 2β-(4-morpholinyl)-16β-(1-pyrrolidinyl)-5α-androstan-3α-ol-17β-acetate (Compound VIII), about 1.3 to about 3 equivalents of allyl bromide per mole of Compound VIII, and a polar aprotic organic solvent selected from a group consisting of: halogenated hydrocarbons, esters, ketones and mixtures thereof, wherein their water content is of less than about 0.05% by KF, and an inorganic base selected from a group consisting of: aluminum oxide, sodium carbonate, sodium bicarbonate and potassium carbonate; isolating Rocuronium bromide; dissolving Rocuronium bromide of formula I in a polar aprotic organic solvent selected from a group consisting of: halogenated hydrocarbons, esters, ketones, and mixtures thereof; removing the polar aprotic organic solvent at a temperature below about 25° C. to obtain an oily residue; dissolving the oily residue in a polar aprotic organic solvent selected from a group consisting of: halogenated hydrocarbons, esters, ketones and mixtures thereof; adding a decolorizing agent selected from a group consisting of: aluminum oxide, activated charcoal and silica gel optionally combined with a base selected from a group consisting of: sodium carbonate, sodium bicarbonate and potassium carbonate; filtering; adding the filtrate to an anti-solvent selected from a group consisting of: halogenated hydrocarbons, ethers, esters, aromatic hydrocarbons and mixtures thereof; stirring at about 840 rpm to 1000 rpm to obtain a suspension; recovering the wet solid of Rocuronium bromide of formula I; and drying the Rocuronium bromide at a temperature of no more than about 35° C.

Rocuronium bromide with a potentiometrical assay from 99 to 101% in acetic acid and perchloric acid, with about 0.07% area to about 0.02% area by HPLC of impurity A, and with at least one of the solvents ethyl ether and dichloromethane in an amount of equal or less than about 850 ppm, and 600 ppm, respectively, can be prepared by combining 2β-(4-morpholinyl)-16β-(1-pyrrolidinyl)-5α-androstan-3α-ol-17β-acetate (Compound VIII), about 2 equivalents of allyl bromide per mole of Compound VIII, and a polar aprotic organic solvent selected from a group consisting of: dichloromethane, ethylacetate, acetone and mixtures thereof, wherein their water content is of less than about 0.03% by KF, and an inorganic base selected from a group consisting of: aluminum oxide, sodium carbonate, sodium bicarbonate and potassium carbonate; isolating Rocuronium bromide; dissolving Rocuronium bromide of formula I in a polar aprotic organic solvent selected from a group consisting of: dichloromethane, ethylacetate, acetone, and mixtures thereof, removing the polar aprotic organic solvent at a temperature below about 25° C. to obtain an oily residue; dissolving the oily residue in a polar aprotic organic solvent selected from a group consisting of: dichloromethane, ethylacetate, acetone and mixtures thereof; adding a decolorizing agent selected from a group consisting of: aluminum oxide, activated charcoal and silica gel optionally combined with a base selected from a group consisting of: sodium carbonate, sodium bicarbonate and potassium carbonate; filtering; adding the filtrate to an anti-solvent selected from a group consisting of: dichloromethane, diethyl ether, diisopropylether, ethylacetate, toluene and mixtures thereof; stirring at about 840 rpm to 1000 rpm to obtain a suspension; recovering the wet solid of Rocuronium bromide of formula I; and drying the Rocuronium bromide at a temperature of no more than about 35° C.

Preferably, 2β-(4-morpholinyl)-16β-(1-pyrrolidinyl)-5α-androstan-3α-ol-17β-acetate is dissolved in a polar aprotic organic solvent, prior to combining with allyl bromide and the inorganic base. Thereafter, ⅓ of the solvent volume is removed at a temperature below about 35° C. to obtain a solution with less than about 0.1% water content as measured by Karl Fisher. This step may be repeated at least twice. Preferably, the solvent is removed by distillation. Optionally, the step of adding a solvent and removing it may be replaced by using conventional methods known in the art, which can allow a water content as determined by Karl Fischer of less than about 0.1%. Preferably, the mixture of compound VIII, polar aprotic organic solvent and the allyl bromide has a low water content, more preferably, of less than about 0.1% water content by Karl Fischer, more preferably, of less than about 0.05% water content by Karl Fischer, and most preferably, of less than about 0.03% water content by Karl Fischer.

Optionally, the Compound VIII, allyl bromide and the polar aprotic organic solvent can be treated separately with an inorganic base, prior to combining them. Preferably, the inorganic base is added when combining the reacting substances. The addition of the base avoids competing reactions leading to undesired side products, such as the protonated species (Formula 1)

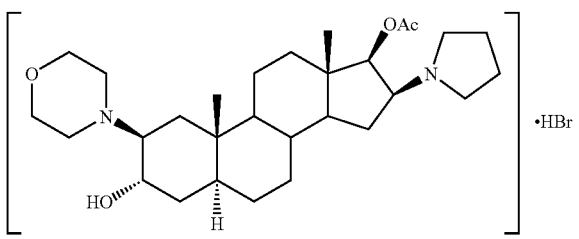

Preferably, 2 equivalents of allyl bromide per mole of Compound VIII is used.

Preferably, the mixture obtained after combining Compound VII, a polar aprotic organic solvent, about 1.3 to about 3 equivalents of allyl bromide and an inorganic base is stirred at a temperature of about 15° C. to about 40° C., more preferably, at a temperature of about 35° C. to about 40° C.

Preferably, the mixture is stirred for about 20 hours to about 24 hours. More preferably, the mixture is stirred for about 22 hours to about 24 hours.

The polar aprotic organic solvent is selected from a group consisting of: halogenated hydrocarbons, esters, ketones and mixtures thereof. Preferably, the halogenated hydrocarbon is dichloromethane. A preferred ester is ethylacetate. Preferably, the ketone is acetone. More preferably, the polar aprotic organic solvent is dichloromethane.

Inorganic bases include, but are not limited to, aluminum oxide, sodium carbonate, sodium bicarbonate, or potassium carbonate. Preferably, the inorganic base is sodium carbonate.

Preferably, after isolating Rocuronium bromide it is dissolved in a polar aprotic organic solvent, and the solvent is removed to obtain an oily residue. Dissolution and evaporation can be repeated as many times required to remove excess of ally bromide.

The decolorizing agent includes, but is not limited to, aluminum oxide, activated charcoal or silica gel. When the decolorizing agent is not basic then a base may be used in combination with the decolorizing agent. Preferably, the decolorizing agent is aluminum oxide. Preferably, the base is sodium bicarbonate.

The filtration may be performed using any method commonly used in the art. Typically, the filtration is performed in a close filter equipped with a nitrogen inlet and vacuum. Preferably, after filtration, the filtrate is added to the anti-solvent at an addition flow of about 0.55 to about 0.610 L/min, and preferably, of about 0.58 L/min.

Preferably, the addition of the filtrate to the anti-solvent is done while stirring vigorously to avoid a high content of residual solvents in rocuronium bromide. Preferably, the stirring is done at a rate of about 840 rpm. Preferably, the anti-solvent is selected from a group consisting of: halogenated hydrocarbons, ethers, esters, aromatic hydrocarbons and mixtures thereof. Preferably, the halogenated hydrocarbon is dichloromethane. A preferred ether is either diethyl ether or diisopropylether. Preferably, the ester is ethylacetate. A preferred aromatic hydrocarbon is toluene. Preferably, the solvent in the filtrate is dichloromethane and the anti-solvent is diethylether. Typically, when the solvent is dichloromethane and anti-solvent is diethylether, the reaction yields about 112% to 118% w/w of rocuronium bromide.

Preferably, rocuronium bromide is dried under vacuum for at least 5 days at a temperature of no more than about 35° C. Not to be limited by theory, however, it is believed that this method of drying is one factor in preventing the formation of impurity A.

Yet another embodiment of the invention encompasses a pharmaceutical formulation comprising substantially pure rocuronium bromide and at least one pharmaceutically acceptable excipient. Selection of excipients and the amounts to use may be readily determined by the formulation scientist based upon experience and consideration of standard procedures and reference works in the field. Excipients may include, but are not limited to, diluents, binders, disintegrants, glidants, lubricants, preservatives, viscosity enhancers, buffering agents, flavoring agents, and coloring agents.

The pharmaceutical formulation may be provided in a solid or liquid dosage form. Solid dosage forms, include, but are not limited to, tablets, powders, capsules, sachets, and troches. Liquid dosage forms, include, but are not limited to, forms suitable for intravenous injection. In liquid dosage forms, the rocuronium bromide and any other solid excipients are dissolved or suspended in a liquid carrier.

In yet another embodiment, the invention encompasses a process for preparing the pharmaceutical formulation comprising mixing substantially pure rocuronium bromide and at least one pharmaceutically acceptable excipient.

In yet another embodiment, the invention encompasses a method of inducing muscle relaxation comprising administering the pharmaceutical formulation to a patient in need thereof.

Having thus described the invention with reference to particular preferred embodiments, those in the art can appreciate modifications to the invention as described and illustrated that do not depart from the spirit and scope of the invention as disclosed in the specification. The following examples are set forth to aid in understanding the invention but are not intended to, and should not be construed to, limit its scope in any way.

EXAMPLES

GC Method for Determining Residual Solvent Content

The gas chromatography method comprises using a column and packing of 6% cianopropilfenil-94% Metilpolisiloxa (Zebron-624, Part No 7HM-G005-31) or equivalent having a length of 30, a diameter of 0.32 mm, and a film thickness of 1.8 μm. The injector temperature was 140° C., detector temperature was 250° C., and the oven was warmed at 50° C. for 20 minutes and then heated to 220° C. at a rate of 15° C./min and held for 2 minutes prior to injecting the sample (injector mode split). A 1 µL injection volume was used and helium at a constant pressure of 5.53 psi was the carrier gas. A FID detector was used with a hydrogen flow of 30 ml/min., and an air flow of 300 ml/min.

The internal standard (ISS) was prepared by mixing 25 µL of benzene to 250 mL with DMSO. Stock solutions were prepared as follows. Stock solution 1: Added 30 mL of ISS and 1 mL of methanol in a 50 mL volumetric flask, dilute to volume with ISS. Stock solution 2: Added 50 mL of ISS to 1 mL of acetonitrile and 1 mL of dichloromethane in a 100 mL volumetric flask, dilute to volume with ISS. Stock solution 3: Added 15 mL of ISS and 4 mL of diethyl ether in a 25 mL volumetric flask, diluted to volume with ISS. The standard stock solution was made by mixing 4 mL of stock solution 1, 1 mL of stock solution 2, 1 mL of stock solution 3 into a 25 mL volumetric flask and diluting to volume with ISS. The following table summarizes the final concentration for each solvent in the standard stock solution.

| Solvent | mg/mL |
| --- | --- |
| Methanol | 2.531 |
| Diethyl ether | 4.544 |
| Acetonitrile | 0.314 |
| Dichlorometane | 0.532 |

The sample solution was prepared by adding 200 mg of sample to 2 mL of ISS. The following table summarizes the retention times (RT) and relative retention times (RRT) of the solvents.

| Solvent | RT | RRT |
| --- | --- | --- |
| Methanol | 6.7' | 0.30 |
| Diethyl ether | 8.7' | 0.39 |
| Acetonitrile | 10.9' | 0.49 |
| Dichloromethane | 11.3' | 0.51 |
| Benzene (IS) | 22.3' | 1.00 |

The sample was injected according to the following sequence: (a) 1 µL of Internal Standard Solution; (b) 1 µL of Working Standard Solution (three times); (c) 1 µL of Internal Standard Solution; (d) 1 µL of sample Solution first preparation; and (e) 1 µL of sample Solution second preparation.

The amount of sample (in ppm) was calculated using the following procedure. Integrate all peaks disregarding peaks of blank and perform the calculation as follows:

$$ppm = \frac{Rspl}{Rstd} \times \frac{Cstd}{Cspl} \times 100 \times 10000$$

wherein,

Rspl is the ratio from peak area of each solvent with the peak area of Internal Standard in the Sample Solution.

Rstd is the ratio from peak area of each solvent with the peak area of Internal Standard in the Working Standard Solution.

Cspl is the Sample concentration.

Cstd is the Standard concentration (mgl/mL)

HPLC Methodology

Each HPLC was performed according to the European Pharmacopoeia 5th edition (Suplement 5.4, pp. 4013-4014).

The following conditions were used:

Test Solution: 0.100 g. of the product to be analyzed was dissolved in the solvent mixture (water:acetonitrile, 10:90 v/v) and diluted to 10.0 mL.

Reference Solution: 1.0 mL of the test solution was diluted to 100.0 mL with the solvent mixture (water:acetonitrile, 10:90 v/v). 1.0 mL of this solution was diluted to 10.0 mL with the mobile phase.

Column: Hypersil Silica 5 µm, 250×4.6 mm.

Temperature: 30° C.

Mobile Phase Mixture of 100 parts (v/v) of a solution made with 4.53 g of tetramethylammonium hydroxide, adjusted to pH 7.4, and 900 parts (v/v) of acetonitrile.

Flow Rate: 2.0 ml/min.

Detection: .UV operated at 210 nm.

Injection volume: 5 µl.

Run time: 2.5 times the retention time of the rocuronium.

Limits:

The impurity peak area was multiplied by the corresponding correcting factor: Compound VIII correcting factor=0.47.

Assay Methodology 0.400 g in 40 ml of glacial acetic acid R, titrate was dissolved in 0.1 M perchloric acid R. The end-point is determined potentiometrically.

Comparative Example 1

Preparation of 1-[17β-acetyloxy-3α-hydroxy-2β-(4-morpholinyl)-5α-androstan-16β-yl]-1(2-propenyl) pyrrolidinium bromide, Compound I, According to Example 23 of U.S. Pat. No. 4,894,369

Allyl bromide (1.95 mL) was added to a solution of (2β,3α,5α,16β,17β,)-2-(4-morpholinyl)-16-(1-pyrrolidinyl)-andostane-3,17-diol 17-acetate (1.35 g, 2.76 mmol) in dichloromethane (27 mL) and the solution was sealed in a pressure bottle (125 mL capacity) at room temperature for 22 h (IP by TLC). The solvent was removed under reduced pressure at 15° C. and the crude solid (2.44 g) was chromatographed on alumina (Fluka type 5016A) and eluted with dichloromethane. The pure fractions were combined, concentrated by solvent evaporation, and taken up in dichloromethane (15 mL). Diethyl ether (100 mL) was added at 20° C. to precipitate pure rocuronium bromide, which was collected by filtration under a nitrogen atmosphere and washed with diethyl ether (13.5 mL). The obtained compound was dried under vacuum at 32-33° C. during 5 days. The product was milled after 17 h, then continuously dried to afford 1.15 g (1.88 mmol, 85.2% w/w yield, 68.1% molar yield) of a light cream solid.

Dried Melting point=208° C., Dried $[\alpha]_D^{20}$+29.0° (c=According to PharmaEurope method). U.S. Pat. No. 4,894,369 Melting Point=161-169° C., $[\alpha]_D^{20}$+18.7° (c=1.03 in $CHCl_3$). Purity by HPLC: 99.61%. Impurity A: 0.1% area. Residual solvents: methanol not detected, ethyl ether 16519 ppm, acetonitrile not detected, dichloromethane 176 ppm.

Example 2

Preparation of 1-[17β-acetyloxy-3α-hydroxy-2β-(4-morpholinyl)-5α-androstan-16β-yl]-1(2-propenyl) pyrrolidinium bromide, Compound I A 185 L glass reactor equipped with stirring anchor type (1750-840 rpm) was charged with 2β-(4-morpholinyl)-16β-(1-pyrrolidinyl)-5α-androstan-3α,17β-diol 17-acetate (Compound VIII) (8.65 Kg, 17.7 mol) and dichloromethane (130 L) at 20-22° C. under N₂ atmosphere. Then, 40 L of dichloromethane were distilled at 32-35° C. at atmospheric pressure and the solution was allowed to reach 20-25° C. The volume was replaced with 40 L of dichloromethane and the same volume was stripped at 32-35° C., the mixture was cooled down to 20-25° C. Sodium carbonate (8.65 Kg) was added into the reactor and the resulting mixture was stirred (840 rpm) during 5 min., followed by the addition of allyl bromide (4.3 Kg, 35.5 mol). The resulting suspension was stirred (840 rpm) for 24 hours at 32-35° C. The mixture was then cooled to room temperature (20-25° C.) and filtered in a housing filter under vacuum (11 mm Hg) to remove the salt which was rinsed with dichloromethane (8.65 L). The solvent mixture was removed under vacuum keeping the temperature below 20° C. The oily product obtained was dissolved with dichloromethane (45 L) and concentrated under vacuum keeping the temperature below 20° C.; this procedure was repeated twice. Once again the residue was dissolved at room temperature under nitrogen atmosphere in dichloromethane (86.5 L) and aluminum oxide (4.3 Kg) was added. The resulting mixture was stirred at 20-22° C. during 30 min and then filtered. The solution (52.77 L) was slowly added (90 min.) toward the breakwater (flow 0.58 L/min) to a 1500 L glass reactor equipped with stirring propeller type (1680 rpm) containing diethyl ether (452 L) at 20-22° C. while continuously stirring (840 rpm). The resulting suspension was stirred (840 rpm) for 30 minutes and the solid was filtered off in a close filter under nitrogen atmosphere (2 Kg/m² max.), washed with diethyl ether (2×3 L) and drained for at least 24 h. The solid obtained was dried under vacuum (11 mm Hg) at 35° C. for at least during 5 days to give 9.70 Kg (0.016 mol, 112.13% w/w yield, 89.88% molar yield) of an off-white solid. The humid melting point was 218° C., the Humid $[\alpha]_D^{20}$+17.9° (c=1.0 in CHCl₃). The melting point of the dried material was 210° C., dried $[\alpha]_D^{20}$+18.9° (c=1.0 in CHCl₃).

The purity by HPLC was 99.9% by area and Impurity A was present as 0.07% area. The residual solvents present were methanol (30 ppm), ethyl ether (850 ppm), acetonitrile (27 ppm), and dichloromethane (19 ppm).

Example 3

Preparation of 1-[17β-acetyloxy-3α-hydroxy-2β-(4-morpholinyl)-5α-androstan-16β-yl]-1-(2-propenyl) pyrrolidinium bromide, Compound I, Base In Situ In a three neck flask equipped with heated mantle, thermometer and magnetic stirrer, was charged dichloromethane (20 mL), sodium carbonate (2.0 g, 0.081 mol) and slowly allyl bromide (0.692 mL, 0.00818 mol) at 20-22° C. under N₂ atmosphere. The mixture was stirred during 5 min and 2β-(4-morpholinyl)-16β-(1-pyrrolidinyl)-5α-androstan-3α,17β-diol 17-acetate (Compound VIII) (2.0 g, 4.09×10⁻³ mol) was added. The resulting mixture was stirred during 5-10 min. The resulting solution was stirred under reflux for 22 hours. The mixture was then cooled to room temperature (20-25° C.) and filtered (membrane 0.45 microns) under nitrogen atmosphere. The solvent was removed under vacuum keeping the temperature below 20° C. The foam obtained was dissolved with dichloromethane (10 mL) and concentrated under vacuum keeping the temperature below 20° C.; this procedure was repeated twice. Once again the residue was dissolved at room temperature under nitrogen atmosphere in dichloromethane (22 mL).

The mixture was divided in two portions (11 mL each); one of them was treated with alumina (1.0 g), stirred for 30 min and then filtered (membrane 0.45 microns). The solution was slowly added to a flask containing diethyl ether (74 mL) with continuous vigorous stirring. The resulting suspension was stirred for 30 minutes at 20-25° C., filtered under nitrogen atmosphere, and washed with ethyl ether (10 mL). The solid obtained was drained under vacuum and nitrogen atmosphere for 10-15 min, dried at 40° C. at least during 40 h to give 1.04 g (1.70×10⁻³ mol, 104% w/w yield, 83.1% molar yield) of an off-white solid, having a purity of 99.86% area (correction factor included) by HPLC, containing impurity A 0.02% area (correction factor included) by HPLC.

What is claimed is:

1. Rocuronium bromide, Compound I:

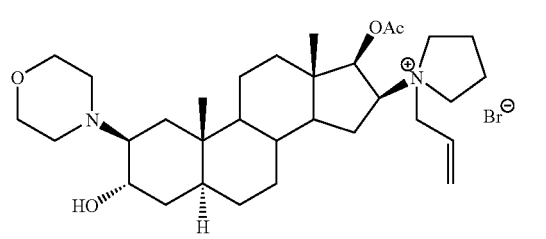

having:
(a) a potentiometrical assay of from 99% to 101% in acetic acid and perchloric acid;
(b) less than about 0.2% area by HPLC of 2β-(4-morpholinyl)-16β-(1-pyrrolidinyl)-5α-androstan-3α-ol-17β-acetate; and having
(c) at least one of the solvents ethyl ether and dichloromethane in an amount equal to or less than about 850 ppm, and 600 ppm, respectively.

2. The rocuronium bromide of claim 1, having less than about 0.1% area by HPLC of 2β-(4-morpholinyl)-16β-(1-pyrrolidinyl)-5α-androstan-3α-ol-17β-acetate.

3. The rocuronium bromide of claim 1, having about 0.1% area to about 0.02% area by HPLC of 2β-(4-morpholinyl)-16β-(1-pyrrolidinyl)-5α-androstan-3α-ol-17β-acetate.

4. The rocuronium bromide of claim 1, having about 0.07% area to about 0.02% area by HPLC of 2β-(4-morpholinyl)-16β-(1-pyrrolidinyl)-5α-androstan-3α-ol-17β-acetate.

5. The rocuronium bromide of claim 1, having a total solvent content of less than 2000 ppm.

6. A pharmaceutical formulation comprising the rocuronium bromide of claim 1, and at least one pharmaceutically acceptable excipient.

7. A process for preparing the pharmaceutical formulation of claim 6 comprising mixing the rocuronium bromide and the at least one pharmaceutically acceptable excipient.

8. A method of inducing muscle relaxation comprising administering the pharmaceutical formulation of claim 6 to a patient in need thereof.

* * * * *